US012613213B2

(12) United States Patent
Wieder

(10) Patent No.: US 12,613,213 B2
(45) Date of Patent: Apr. 28, 2026

(54) GALVANICALLY FUNCTIONALIZED SENSORS

(71) Applicant: Roche Diabetes Care, Inc., Indianapolis, IN (US)

(72) Inventor: Herbert Wieder, Mannheim (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 307 days.

(21) Appl. No.: 18/186,544

(22) Filed: Mar. 20, 2023

(65) Prior Publication Data

US 2023/0221277 A1 Jul. 13, 2023

Related U.S. Application Data

(62) Division of application No. 16/308,579, filed as application No. PCT/EP2017/065943 on Jun. 28, 2017, now abandoned.

(51) Int. Cl.
| | |
|---|---|
| *G01N 27/327* | (2006.01) |
| *A61B 5/145* | (2006.01) |
| *A61B 5/1468* | (2006.01) |
| *A61B 5/1486* | (2006.01) |
| *C12Q 1/00* | (2006.01) |
| *C12Q 1/28* | (2006.01) |

(52) U.S. Cl.
CPC ..... *G01N 27/3272* (2013.01); *A61B 5/14532* (2013.01); *A61B 5/1468* (2013.01); *A61B 5/1486* (2013.01); *C12Q 1/004* (2013.01); *C12Q 1/006* (2013.01); *C12Q 1/28* (2013.01)

(58) Field of Classification Search
None
See application file for complete search history.

(56) References Cited

U.S. PATENT DOCUMENTS

| | | | |
|---|---|---|---|
| 6,071,391 A | 6/2000 | Gotoh et al. | |
| 2004/0007461 A1 | 1/2004 | Edelbrock et al. | |
| 2007/0227907 A1 | 10/2007 | Shah et al. | |
| 2009/0156920 A1* | 6/2009 | Kotzan ................. | C12Q 1/006 |
| | | | 600/347 |
| 2009/0178923 A1 | 7/2009 | Marquant et al. | |
| 2009/0198117 A1 | 8/2009 | Cooper et al. | |
| 2010/0331728 A1 | 12/2010 | Zhang et al. | |
| 2011/0021889 A1 | 1/2011 | Hoss et al. | |
| 2011/0048972 A1 | 3/2011 | Moffat et al. | |
| 2011/0144915 A1 | 6/2011 | Rodgers et al. | |
| 2011/0196216 A1 | 8/2011 | Quarder et al. | |
| 2014/0018653 A1* | 1/2014 | Staib ................. | G01N 27/3272 |
| | | | 600/347 |
| 2015/0099954 A1 | 4/2015 | Achmann et al. | |

FOREIGN PATENT DOCUMENTS

| | | |
|---|---|---|
| EP | 0 366 209 | 5/1990 |
| RU | 2419785 | 5/2011 |
| WO | WO 2005/078424 A1 | 8/2005 |
| WO | WO 2007/071562 A1 | 6/2007 |
| WO | WO 2014/116293 A1 | 7/2014 |

OTHER PUBLICATIONS

Hocevar, S. B., et al. "Glocose microbiosensor based on MnO2 and glucose oxidase modified carbon fiber microeletrode", Electroanalysis, vol. 16, issue 20, (Oct. 21, 2004), pp. 1711-1716. Retrieved online. DOI < 10.1002/elan.200303019.

Rachna Rawal et al: "An amperometric biosensor based on laccase immobilized onto MnO2NPs/cMWCNT/PANI modified Au electrode", International Journal of Biological Macromolecules, vol. 51, No. 1-2, 2012, pp. 175-181.

Schachl, K., Alemu, H. et al., Amperometric determination of hydrogen peroxide with a manganese dioxide film-modified screen printed electrode. Fresenius J. Anal. Chem, 362, 1998.

Yu et al: "A facile and practical biosensor for choline based on maganese dioxide nanoparticles synthesized in-situ at the surface of elctrode by one-step electrodeposition", TALANTA, vol. 146, Jun. 19, 2015, pp. 707-713.

* cited by examiner

*Primary Examiner* — J. Christopher Ball
*Assistant Examiner* — John C Ball
(74) *Attorney, Agent, or Firm* — Woodard, Emhardt, Henry, Reeves & Wagner, LLP

(57) ABSTRACT

The present invention relates to a biosensor for determining an analyte comprising a substrate, a working electrode comprising an electrically conductive pad in conductive contact with a mediator layer, and an enzyme layer in diffusion-enabling contact with said mediator layer, wherein said mediator layer is an electrodeposited mediator layer, and wherein said mediator layer comprises, in an embodiment consists of, an electrocatalytic agent. The present invention further relates to a method for manufacturing a biosensor, comprising providing a substrate having at least one conductive pad, electrodepositing a mediator layer onto at least part of said conductive pad, wherein said mediator layer comprises, in an embodiment consists of, an electrocatalytic agent, and depositing an enzyme layer onto at least part of said mediator layer. Moreover, the present invention relates to uses and methods related to the biosensor of the present invention.

10 Claims, 2 Drawing Sheets

GALVANICALLY FUNCTIONALIZED SENSORS

Figure 1:
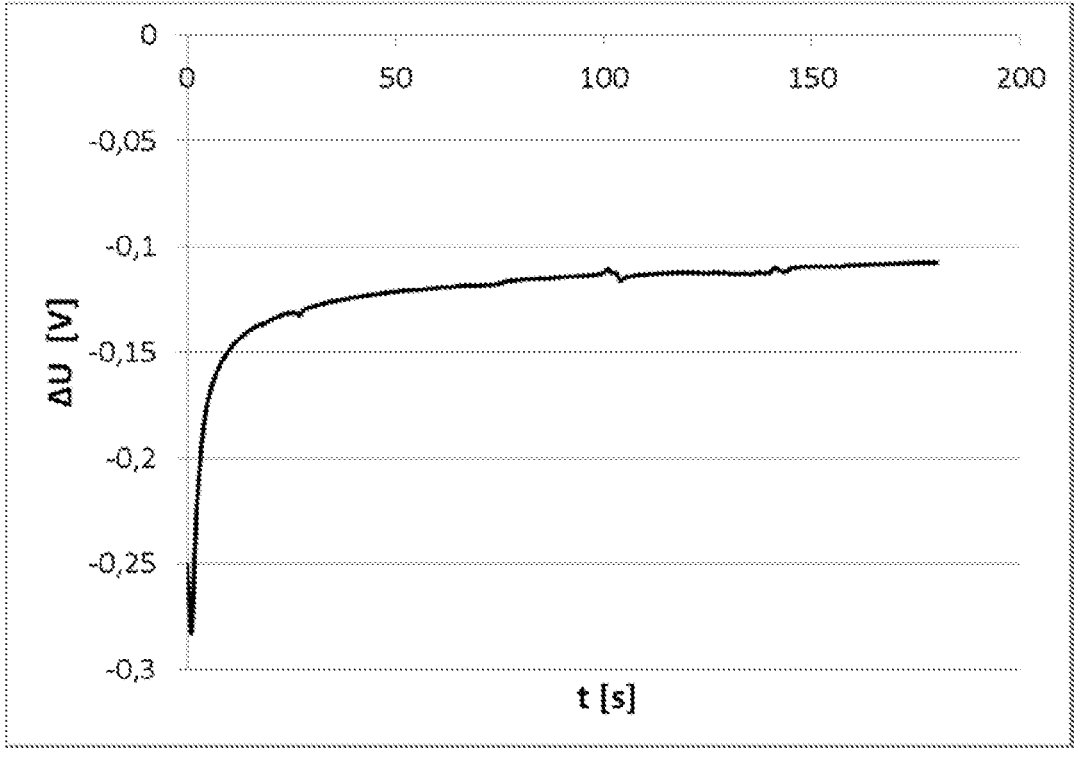

The present invention relates to a biosensor for determining an analyte comprising a substrate, a working electrode comprising an electrically conductive pad in conductive contact with a mediator layer, and an enzyme layer in diffusion-enabling contact with said mediator layer, wherein said mediator layer is an electrodeposited mediator layer, and wherein said mediator layer comprises, in an embodiment consists of, an electrocatalytic agent. The present invention further relates to a method for manufacturing a biosensor, comprising providing a substrate having at least one conductive pad, electrodepositing a mediator layer onto at least part of said conductive pad, wherein said mediator layer comprises, in an embodiment consists of, an electrocatalytic agent, and depositing an enzyme layer onto at least part of said mediator layer. Moreover, the present invention relates to uses and methods related to the biosensor of the present invention.

The determination of the concentration of one or more analytes such as glucose, in one or more body fluids, such as interstitial fluid and/or blood, is an essential component of therapy and/or prevention in many diseases. Specifically, the determination of blood glucose concentration as well as a corresponding medication is an essential part of daily routine for many diabetics. In order to increase convenience and in order to avoid restricting the daily routine by more than a tolerable degree, portable devices are known in the art, such as for measuring blood glucose concentration, during work, leisure or other activities away from home. Specifically, electrochemical measurement techniques are known using sensors which are fully or partially implantable into a body tissue of the user and which are capable of providing continuous or discontinuous measurements of the analyte concentration. Examples of these types of implantable sensor elements are disclosed in WO 2007/071562 A1, US 2011/0021889 A1, US 2010/0230285 A1, WO 2005/078424 A1 or by international patent application PCT/EP2011/072732.

Test elements for electrochemically detecting the concentration of at least one analyte in a body fluid, such as for determining a blood glucose concentration in blood and/or interstitial fluid, typically comprise at least one working electrode as well as at least one counter electrode. In addition, optionally, the sensor element may comprise at least one reference electrode. However, in alternative embodiments, a reference electrode may be omitted and/or may be combined with the counter electrode. For potential electrode materials, both for the working electrode and the counter electrode, as well as for potential electrochemical measurement setups for determining the analyte concentration by using corresponding amperometric setups, reference may be made to WO 2007/071562 A1. However, other types of measurement setups are possible, in order to derive an analyte concentration from a comparison of electrode potentials.

In typical electrochemical sensor setups, the counter electrode is provided in order to close the electric circuit to the working electrode. For this purpose, typically, redox currents and/or, to a lower extent, capacitive charging currents are used. Typically, the working electrode comprises at least one detector substance adapted to perform an oxidation reaction or a reduction reaction with the analyte. In many cases, the detector substance comprises at least one enzyme such as glucose oxidase (GOD). In case the detection reaction comprises an oxidation reaction at the working electrode, the counter electrode typically provides a reduction reaction in order to close the electric circuit. Effective oxidation or reduction of an analyte may require a high overpotential, which carries the danger of inducing undesirable side reactions. Accordingly, catalysts (mediators), which may in principle be biological catalysts (enzymes) or inorganic catalysts, are typically included in the architecture of working electrodes. E.g., $MnO_2$ has been used as an electrocatalyst for the oxidation of peroxides, in particular of hydrogen peroxide $(H_2O_2)$. Moreover, in order to increase signal strength, attempts at increasing electrode surface have been made, e.g. by electroplating several layers of metal as proposed in US 2007/227907 A1.

Various electrode setups are known in the art. Thus, in US 2009/0198117 A1, an analyte sensor apparatus for implantation within a mammal is disclosed. The analyte sensor apparatus comprises a base layer, a conductive layer disposed on the base layer, an analyte sensing layer and an analyte modulation layer disposed on the analyte sensing layer. The conductive layer includes a working electrode which comprises a plurality of conductive nanotubes. The analyte sensing layer comprises an oxidoreductase disposed on the conductive nanotubes. The oxidoreductase generates hydrogen peroxide in the presence of an analyte to be sensed. The analyte modulating layer modulates the diffusion of the analyte therethrough.

As mentioned above, a plurality of electrode combinations is known. Thus, in three electrode setups, besides the working electrode and the counter electrode, at least one reference electrode is provided, independently from the counter electrode. The potential of the counter electrode, in this case, typically may be adjusted independently from the potential of the reference electrode. As explained in more detail in WO 2007/071562 A1, a potentiostatic controller may be provided, which, on one hand, provides a desired potential difference or voltage between the working electrode and the reference electrode and, on the other hand, is adapted such that a current of the detection reaction taking place at the working electrode is balanced by an appropriate counter process at the counter electrode, thereby closing the electric circuit. For the latter purpose, the counter electrode has to be adjusted to a potential at which the appropriate and required current is generated by an appropriate electrode reaction at the counter electrode.

Thus, the process taking place at the counter electrode may be compared to the process of galvanostatic potentiometry. The counter electrode generally will attain a potential at which the redox process generates the required current. In case this redox process of one redox system is insufficient for providing an appropriate current, the reaction partners will diminish and the counter electrode will proceed to a potential of a subsequent redox reaction, until the sum of all partial currents is sufficient for generating an appropriate counter current for balancing the detection reaction of the working electrode.

The potential of the counter electrode as well as the electrode reactions at the counter electrode will typically depend on a plurality of factors. Thus, the surface of the counter electrode itself will have an influence, such as the surface area, the roughness of the electrode and/or other surface properties. Further, the presence of redox species and the respective overpotential at the counter electrode will influence the above-mentioned properties of the counter electrode, as well as the concentration of the redox species and the redox potential and overvoltage of the process.

Specifically in the case of in-vivo continuous monitoring sensors, these sensors will typically be surrounded by blood and/or interstitial fluid. As mentioned above, most known biosensors are using oxidation detection reactions at the working electrode in which the analyte, such as glucose, is oxidized. As an example, glucose will enzymatically be oxidized, and reduced co-products will be generated, such as $H_2O_2$. Since most constituents of blood and interstitial fluid are present in a reduced form, the number of reducible species in typical in-vivo measurements is limited. In the order of their respective redox potentials, the following reducible species may be named as examples: oxygen, $H_2O_2$, $H_2O$. The amount of oxygen is typically rather limited, specifically in in-vivo measurements, specifically in interstitial fluid. By encapsulation of the sensor element implanted into the body tissue, a delivery of oxygen to the working electrode may further diminish over time. $H_2O_2$ may be generated by electrode reaction, such as by reduction of $O_2$ and/or by enzymatic reaction. $H_2O$ typically is widely available at high concentrations. However, using water as a reducible species typically includes a formation of $H_2$-gas. This gas formation may lead to a de-wetting of the electrode, which, typically, will increase the above-mentioned effects. Further, the formation of gas may lead to a lift-off of a membrane which typically covers the working electrode and may even lead to a full removal of the membrane and/or the electrode.

Typically, in-vivo sensors are produced by providing a support including appropriate electrical leads to provide for the required electrodes and by screen printing a paste comprising a reference chemistry for the reference electrode and a paste comprising the reaction chemistry for the working electrode in two separate processes, e.g. screen printing processes, cf. e.g. US 2004/007461 A1. This procedure requires labor-intensive quality control of reagents and their mixtures. Moreover, the screen printing processes require several drying steps and, as such, are error prone by producing sensors which are incompletely printed or from which part of the layer applied has chipped off, in particular if a flexible support is used. Moreover, the screen printing process requires the presence of solvents, of which trace amounts may remain after drying and which may interfere with measurement. In particular, a frequently used solvent, diethylene-glycol monobutyl ether (DEGMBE), is difficult to remove entirely and may become peroxidized during manufacture, which typically causes interference in sensors detecting peroxides, e.g. glucose sensors using the glucose oxidase/$H_2O_2$ chemistry. Further, by screen printing a reaction chemistry, enzyme (e.g. glucose oxidase) and mediator (e.g. $MnO_2$ used for catalyzing oxidation of $H_2O_2$), though dispersed, typically are present in the reaction chemistry as aggregates, such that $H_2O_2$ must first diffuse from an enzyme aggregate to an $MnO_2$ aggregate for detection, which decreases speed and sensitivity of detection by decreasing capture efficiency.

As alternative architecture for a working electrode, it was proposed to electrodeposit onto the electrode metal first a layer of metal including an enzyme, and as a further layer electroplating a mediator of electron transfer (EP 0 368 209 A1).

Problem to be Solved

It is therefore an objective of the present invention to provide a biosensor, which may be at least partially implantable into a body tissue, which fully or partially avoids the short-comings of known sensor elements as discussed above. In particular, the sensor element shall provide improvements regarding the problems related to screen-printing of reaction chemistries and/or reference chemistries.

SUMMARY OF THE INVENTION

This problem is solved by a biosensor and related methods with the features of the independent claims. Preferred embodiments of the biosensor and method for manufacturing the biosensor are disclosed in the specification and in the dependent claims.

Accordingly, the present invention relates to a biosensor for determining an analyte comprising a substrate, a working electrode comprising an electrically conductive pad in conductive contact with a mediator layer, and an enzyme layer in diffusion-enabling contact with said mediator layer, wherein said mediator layer is an electrodeposited mediator layer, and wherein said mediator layer comprises an electrocatalytic agent.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which a solely and exclusively consists of B) and to a situation in which, besides B, one or more further elements are present in entity A, such as element C, elements C and D or even further elements.

Further, as used in the following, the terms "preferably", "more preferably", "most preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention. Moreover, if not otherwise indicated, the term "about" relates to the indicated value with the commonly accepted technical precision in the relevant field, in an embodiment relates to the indicated value ±20%.

The term "biosensor", as used herein, relates to a device comprising the means as indicated herein. In an embodiment, the biosensor comprises a substrate, a working electrode in conductive contact with a mediator layer, and an enzyme layer in diffusion-enabling contact with said mediator layer, as described elsewhere herein, respectively.

In an embodiment, the biosensor is an implantable biosensor. Thus, in an embodiment, the biosensor further comprises a diffusion membrane and/or a biocompatibility layer. The term "diffusion membrane", as used herein, relates to a polymer permitting diffusion of the analyte, in particular with a thickness of from 1 μm to 100 μm, in an embodiment of from 2.5 μm to 50 μm. In an embodiment, the diffusion membrane comprises or consists of a biocompatible polymer, in particular a polymer produced by polymerizing butyl-methacrylate (BUMA) and/or 2-hydroxyethylmethacrylate (HEMA) monomers. In a further embodiment, the diffusion membrane permits diffusion of the analyte, but not of high-molecular constituents comprised in an analysis fluid, e.g. a bodily fluid. Accordingly, the diffusion membrane, in an embodiment, specifically permits diffusion of molecules with a molecular weight of less than 10 kDa, in an embodiment less than 5 kDa, in a further embodiment less than 1 kDa. Thus, in an embodiment, the diffusion membrane is semipermeable membrane, in particular a dialysis membrane, in an embodiment a biocompatible dialysis membrane. The term "biocompatibility layer", as used herein, relates to an outmost layer of a biosensor comprising or consisting of a biocompatible material. In an embodiment, the biocompatible material is a material not inducing a bodily response, e.g. an inert material. In an embodiment, the biosensor is completely covered by the biocompatibility layer, with the exception of an aperture covered by a diffusion membrane. In a further embodiment, the biosensor is completely covered by the biocompatibility layer. In an embodiment, said aperture is located in the vicinity of the working electrode and the diffusion membrane separates the working electrode, the mediator layer, and the enzyme layer from the analysis fluid. Moreover, in particular in case the biosensor is an implantable biosensor, the biosensor typically may comprise further electric and electronic means, including, e.g. an energy source, like a battery, and/or a communication unit for exchanging information with an external device, e.g. for reporting measured values of an analyte. Suitable means for providing energy sources and communication units are well-known in the art.

It will be understood that the biosensor may comprise further means as found appropriate by the skilled artisan. In an embodiment, the biosensor is an electrochemical biosensor; thus, the biosensor may comprise further electrical leads and contacts. In an embodiment, the biosensor comprises further electrodes, which may be electrodes having the features as described, or may be electrodes structurally and/or functionally different therefrom. Further electrodes may, e.g. be adapted for use as a filling control, as a temperature sensor, and the like. In an embodiment, the biosensor further comprises a counter electrode, in a further embodiment further comprises a reference electrode and a counter electrode. It is known in the art that biosensor may comprise three electrodes, of which one each is a working electrode, a counter electrode, and a reference electrode ("three-electrode setup"); or the biosensor may comprise two electrodes of which one is a working electrode and the second is a counter electrode and reference electrode ("two-electrode setup"). As indicated above, the biosensor may also comprise further electrodes.

The term "analyte", as used herein, relates to a chemical compound present in a liquid, in particular a bodily liquid. In an embodiment, the liquid is a test sample as specified elsewhere herein. In an embodiment, the analyte is an organic molecule, in a further embodiment, an organic molecule capable of undergoing a redox reaction in the presence of the enzyme according to the present invention. In an embodiment, the analyte is a molecule of a subject's metabolism, i.e. a molecule produced by and/or consumed in at least one chemical reaction taking place in at least one tissue of said subject. Also in an embodiment, the analyte is a low molecular weight chemical compound, in a further embodiment, a chemical compound with a molecular mass of less than 5000 u (5000 Da; 1 u=1.66×10−27 kg), in a further embodiment, less than 1000 u, in a further embodiment, less than 500 u. I.e., in an embodiment, the analyte is not a biological macromolecule. In a further embodiment, the analyte is selected from the list consisting of malate, ethanol, ascorbic acid, cholesterol, glycerol, urea, 3-hydroxybutyrate, lactate, pyruvate, ketones, creatinine, and the like; still in a further embodiment, the analyte is glucose.

The terms "sample" and "test sample", as used herein, refer to a sample of a body fluid, to a sample of separated cells or to a sample from a tissue or an organ or to a sample of wash/rinse fluid obtained from an outer or inner body surface. In an embodiment, the sample is a sample from a body fluid. As used herein, the term "body fluid" relates to all bodily fluids of a subject known to comprise or suspected to comprise the analyte of the present invention, including blood, plasma, interstitial liquid, lacrimal fluid, urine, lymph, cerebrospinal fluid, bile, stool, sweat, and saliva. In an embodiment, the body fluid is blood, serum, or plasma. Samples of body fluids can be obtained by well known techniques including, e.g., venous or arterial puncture, epidermal puncture, and the like. In an embodiment, the bodily liquid is withdrawn from the body of a subject for performing the determination; thus, in an embodiment, the biosensor of the present invention is used in an in vitro method. In a further embodiment, in case the biosensor is an implantable biosensor, the bodily liquid is comprised within a subject; in such case, the bodily liquid, in an embodiment, is blood or interstitial liquid; thus, in a further embodiment, the biosensor of the present invention is used in an in vivo method.

As used herein, the term "substrate" refers to a carrier element (support) which, basically, may have an arbitrary shape, such as a strip-shape. Useful materials and geometries are known in the art. In an embodiment, the substrate is a flexible substrate. In an embodiment, the substrate comprises a layer setup having one, two or more layers, in an embodiment, a flexible layer setup. The substrate may generally be made of any arbitrary substrate material, such as a plastic material and/or a laminate material and/or a paper material and/or a ceramic material. Other materials may be used alternatively or additionally, such as metals or thin-film setups. In an embodiment, the substrate is an insulating layer; thus, in case the substrate is a metal, the metal is, in an embodiment, covered by an insulating layer. In an embodiment, the substrate comprises or consists of flexible PCB or of a polyimide.

The term "electrode" is, in principle, known in the art as relating to an electrical conductor used to make contact with a nonmetallic part of an electrical circuit. The skilled person is aware of a variety of materials and geometries usable as electrodes in a biosensor, e.g. from documents WO 2007/071562 A1, US 2009/0178923 A1, US 2011/0196216 A1, and US 2015/0099954 A1, which are herewith incorporated by reference with regard to their complete disclosure content. In an embodiment, the electrode of the present invention comprises at least one electrically conductive pad and at least one conductive path. The term "conductive pad", as used herein, relates to a small mass of metal forming part of an electrode on which the detection reaction (in case the pad is a pad of a working electrode), a counter reaction (in case the pad is a pad of a counter electrode), or a reference reaction (in case the pad is a pad of a reference electrode) occurs. As used herein, the term "a reaction occurs on a conductive pad of an electrode" relates to a reaction taking place in a layer being in conductive contact, in an embodiment in direct contact, with said conductive pad, e.g. in a mediator layer or in an Ag/AgCl layer. In an embodiment, said at least one electrically conductive pad and/or conductive path consists of a non-corroding material with high conductivity, in particular a noble metal, including gold, silver, platinum, and palladium, or an alloy thereof; or graphite. In an embodiment, the at least one conductive pad and/or conductive path comprises at least one gold layer, in an embodiment consists of gold. As will be understood by the skilled person, the at least one electrically conductive pad and/or conductive path may comprise a multitude of layers, e.g. two or more than two layers. Thus in an embodiment, the at least one conductive pad and/or conductive path of an electrode may comprise a layer of copper and a layer of gold. In an embodiment, the electrode is an electrode manufactured by galvanically depositing a layer of gold onto a copper electrode structure; in an embodiment, said copper electrode structure is generated by lithographically structuring conducting paths onto a substrate. In a further embodiment, the conductive path (electrical lead) conductively connects conductive pad, e.g. to a connector comprised in a measuring device. The conductive pad and the conductive path may, in principle have any geometry deemed appropriate.

In an embodiment, the electrode, in particular a working electrode, is adapted to get in contact with a sample, in particular a body fluid inside a body tissue, either directly or via at least one semipermeable membrane. Thus, in an embodiment, the electrode is arranged such that the electrode gets in contact with at least one electrolyte and/or solvent contained in the body fluid, such as water. The electrode may be or may comprise one or more conductive pads (electrode fields) which fully or partially may be or get in contact with the body fluid. Each electrode field thus may provide at least one interface with the body fluid, e.g. either directly being in contact with a body tissue containing the body fluid or getting into contact with the body fluid via at least one membrane which may fully or partially be permeable for the body fluid or one or more components thereof. One or more of the electrode fields may be contacted via one or more appropriate contact leads, also referred to as conductive paths. Thus, one contact lead or conductive path may electrically contact precisely one electrode or a plurality of two or more electrodes. The at least one electrode, in an embodiment, may have exactly one continuous surface area which may be adapted to get in contact with a body fluid inside the body tissue.

One or more electrodes of the same type may be provided in the biosensor. Each electrode may be contacted electrically by at least one contact lead. In case more than one electrode of the same type is provided, the electrodes may be contacted by one or more contact leads. Thus, two or more electrodes of the same type might be contacted electrically by one and the same contact lead. Alternatively, separate contact leads may be provided for contacting the electrodes, such as at least one separate contact lead per electrode.

Each electrode may be embodied such that an electrochemical reaction may take place at the electrode, wherein the body fluid or a part thereof, such as an electrolyte and/or the analyte, may take place in this electrochemical reaction. Thus, the electrode may be embodied such that an oxidation reaction or a reduction reaction may take place at the electrode.

The biosensor may comprise precisely one working electrode or may comprise a plurality of working electrodes. In case more than one working electrode is provided, at least one of said working electrodes shall comprise an electrically conductive pad in conductive contact with a mediator layer, wherein said mediator layer is an electrodeposited mediator layer, and wherein said mediator layer comprises an electrocatalytic agent. Also, the biosensor may comprise exactly one counter electrode or may comprise a plurality of counter electrodes. In case one or more additional reference electrodes are provided, precisely one reference electrode may be provided or a plurality of reference electrodes may be provided.

In an embodiment, the biosensor is a biosensor for determining an analyte, in particular in a sample. In a further embodiment, said sample is a sample of a subject. The term "determining", as used herein, relates to detecting or measuring the amount of an analyte, in an embodiment, semiquantitatively or, in a further embodiment, quantitatively. In an embodiment, determining comprises estimating the amount of electrons liberated or consumed at a working electrode upon contacting a biosensor according to the present invention with a fluid suspected to comprise an analyte. Methods of estimating the amount of electrons liberated or consumed at a working electrode are known from the prior art. In an embodiment, the amount of electrons liberated or consumed is estimated by means of a potentiostatic measurement.

The term "working electrode" is generally understood as relating to the electrode in an electrochemical cell at which the reaction of interest occurs. According to the present invention, at least one electrically conductive pad of the working electrode is in conductive contact with a mediator layer as specified elsewhere herein. In an embodiment, the working electrode comprises a multiplicity of electrically conductive pads, which are also referred to as electrode fields. In a further embodiment, the multiplicity of electrically conductive pads is a multiplicity of fields as described in US 2011/196216 A1 cited above. In an embodiment, at least one, in an embodiment at least two, in a further embodiment half, in a further embodiment all, of said conductive pads (electrode fields) of the working electrode are in conductive contact with one or more mediator layer (s). In an embodiment, the conductive pads of the working electrode are in conductive contact with the same mediator layer, e.g. by contacting a contiguous mediator layer covering all conductive pads and leads connecting the same. In a further embodiment, conductive pads of one or more working electrodes are in conductive contact with at least two separate or different mediator layers, wherein the term "separate mediator layers" relates to spatially separate mediator layers which are identical in composition, whereas the term "different mediator layers" relates to mediator layers which differ in composition. In an embodiment, a working electrode is an electrode of the biosensor at which the oxidation of a peroxide, in particular of hydrogen peroxide occurs; accordingly, in an embodiment, the working electrode is an anode.

The term "counter electrode" is generally understood as relating to the electrode in an electrochemical cell at which the electrochemical counter-reaction to the reaction of interest occurs; thus, preferably, the counter electrode is the electrode used to close an electrical circuit with the working electrode during measurement. Means and methods of producing a counter electrode are well known in the art, e.g. from the references as cited above. In an embodiment, the counter electrode according to the present invention is located on the opposite side of said substrate relative to the working electrode, in particular as described in US 2015/099954 A1 cited above; in an embodiment, the counter electrode comprises a conductive pad comprising or consisting of gold, which may or may not be further functionalized in such case.

The counter electrode material may further comprise at least one counter electrode redox material adapted to perform at least one redox reaction and/or may comprise one or more electrically conductive materials such as one or more metals. As used herein, the term redox reaction refers to the fact that one partner of the redox reaction is reduced, whereas another partner of the redox reaction is oxidized. Thus, the term redox material refers to a material comprising at least one reducible component and at least one oxidizable component. As an example, the counter electrode redox material may comprise one or more of the following redox systems: Ag/AgCl; Hg/HgCl$_2$, and Mn(II)/Mn(IV). The at least one electrically conductive material may provide at least one electrically conductive surface which, in an embodiment, is an electrically polarizable surface, and which may be adapted such that one or more redox reactions with one or more components contained in the body fluid may take place.

The term "reference electrode" is known to the skilled person to relate to an electrode adapted for providing a known and widely constant electrode potential as a reference potential, in particular by providing a redox system having a known and constant electrode potential. In principle, methods of providing a reference electrode are known to the skilled person, e.g. from the art cited above. In an embodiment, the reference electrode is in conductive contact with a layer of a reference material, in particular a reference material having a known and widely constant electrode potential. In an embodiment, said reference material comprises at least one of the metals silver (Ag), copper (Cu), manganese (Mn), lead (Pb), quicksilver (Hg), nickel (Ni), cobalt (Co), bismuth (Bi), Rhenium (Re), and Tellurium (Te), in an embodiment comprises one of said metals. In an embodiment, the reference material comprises said metal, metals, or alloy thereof in ionic form, in elemental form, or in ionic and elemental form. In a further embodiment, the reference material comprises said metal, metals, or alloy thereof in ionic and elemental form. In an embodiment, the reference material comprises said metal, metals, or alloy thereof in elemental form, and a reference material comprising said metal, metals, or alloy thereof in ionic and elemental form is produced in situ by partially electrochemically oxidizing said elemental form. Thus, in an embodiment, the reference material comprises at least one of said metals in ionic form as an oxide or as a chloride, in a further embodiment comprises at least one of said metals in elemental and in ionic form, in a further embodiment comprises at least one of said metals (i) in elemental form and (ii) as an oxide or as a chloride. In an embodiment, the reference electrode is an Ag/AgCl electrode produced according to standard methods; in a further embodiment, the reference electrode is an Ag/AgCl electrode produced in situ by electrochemically oxidizing silver in the presence of chloride ions.

In an embodiment, the biosensor does not comprise a reference electrode; in particular, in such an embodiment, the biosensor comprises a counter electrode comprising a counter electrode redox material which at the same time functions as a reference material as specified herein above.

In an embodiment, the reference material, in particular the reference material as described herein above, is electrodeposited onto the reference electrode, i.e. in particular by a half-reaction of a galvanic cell. In an embodiment, the reference material, in particular silver, is electrodeposited onto the reference electrode in elemental form and is then partially oxidized to yield a reference material comprising said metal, metals, or alloy thereof in ionic and elemental form. Methods of electrodepositing silver onto a gold electrode are, in principle, known in the art and are further described herein in the Examples below. In an embodiment, silver is electrodeposited from a silver nitrate solution, in particular having a concentration of from 1 μM to saturated at room temperature (25° C.), in an embodiment, of from 100 μM to saturated at room temperature. In an embodiment, deposition is performed potentiostatically, i.e. by applying a constant voltage. The skilled person knows how to determine appropriate voltages for potentiostatic deposition. In an embodiment, a voltage of from −60 mV to −150 mV, in a further embodiment of from −65 mV to −120 mV is applied. In a further embodiment, deposition is performed galvanostatically, i.e. by adjusting the current such that an appropriate deposition rate is achieved, which is, in an embodiment, constant over the deposition time. In an embodiment, galvanostatic deposition is optimized by deriving an optimal current range from a current/potential curve established for the deposition process. As will be understood by the skilled person, the amount of electrodeposited material, in an embodiment layer thickness, can be controlled by adjusting deposition current and/or deposition time.

The term "conductive contact" is understood by the skilled person. In an embodiment, conductive contact is a contact permitting conducting electric charge from a first contact partner to a second contact partner, which may be mediated by an intervening conducting compound, e.g. an electrolyte or, in particular an electron conductor, e.g. a metal. Generally, as used herein, the term "electrically conductive" refers to an electric conductivity σ, typically given in S/m or 1/Ωm of at least $1 \cdot 10^0$ S/m, preferably of at least $1 \cdot 10^3$ S/m and, more preferably, of at least $1 \cdot 10^5$ S/m. As further used herein, the term "electrically insulating" refers to an electric conductivity of no more than $1 \cdot 10^{-1}$ S/m, preferably of no more than $1 \cdot 10^{-2}$ S/m and, most preferably, of no more than $1 \cdot 10^{-5}$ S/m. In a further embodiment, conductive contact is direct contact; thus, in an embodiment, conductive contact between a working electrode and a mediator layer of the present invention is direct contact. I.e. in an embodiment, a conductive pad of a working electrode is at least partially covered by a mediator layer, in particular directly contacting said mediator layer. Correspondingly, in a further embodiment, in an embodiment, conductive contact between a reference electrode and reference material of the present invention is direct contact. I.e. in an embodiment, a conductive pad of a reference electrode is at least partially covered by a reference material, in particular directly contacting said reference material.

Likewise, the term "diffusion-enabling contact", as used herein, relates to contact permitting diffusion of a compound, in particular a compound having a molecular weight as specified for an analyte elsewhere herein, from a first contact partner to a second contact partner. Thus, in an embodiment, diffusion-enabling contact is contact mediated by an intervening composition permitting diffusion of a compound from a first contact partner to a second contact partner. In a further embodiment, diffusion-enabling contact is direct contact; thus, in an embodiment, diffusion-enabling contact between a mediator layer and an enzyme layer is direct contact. I.e. in an embodiment, a mediator layer in conductive contact with a conductive pad of a working electrode is at least partially covered by a reference material, in particular directly contacting said reference material.

As used herein, the term "mediator layer" relates to a layer comprising an electrocatalytic agent. The term "electrocatalytic agent", as used herein, relates to an inorganic chemical compound catalyzing an electrochemical reaction, in particular a reduction reaction or an oxidation reaction at an electrode. In an embodiment, said catalyzing is decreasing the overpotential required for said electrochemical reaction to occur as compared to the uncatalyzed reaction and/or is increasing the rate at which said electrochemical reaction occurs as compared to the uncatalyzed reaction. In particular, "increasing the rate at which said electrochemical reaction occurs" relates to the rate of reaction per area of electrode, in particular per area of working electrode; thus, in an embodiment, electrocatalysis is not increasing the area of an electrode, in particular the area of a working electrode. In an embodiment, the electrocatalytic agent is selective, i.e. the electrocatalytic agent specifically or semi-specifically catalyzes the electrochemical reaction of a specific compound or of a class of compounds, e.g. of peroxides. In an embodiment, the electrocatalytic agent comprises manganese, in a further embodiment manganese ions, in particular manganese-(IV) ions. In an embodiment, the electrocatalytic agent comprises manganese(IV)-oxide ($MnO_2$).

In an embodiment, the mediator layer of the present invention comprises further components, e.g. adherence promoting compounds, one or more metals or alloys as conducting material, or the like. In a further embodiment, the mediator layer of the present invention comprises no components other than the electrocatalytic agent, in particular is free of organic ether peroxides, in an embodiment is free of organic ethers, in a further embodiment is free of organic solvents. In an embodiment, the mediator layer consists of the electrocatalytic agent; thus, in a further embodiment, the mediator layer consists of manganese and/or of $MnO_2$, in a further embodiment consists of $MnO_2$.

In an embodiment, the mediator layer, in particular the electrocatalytic agent as described herein above, is electrodeposited onto the working electrode or working electrodes, i.e. in particular by a half-reaction of a galvanic cell. Methods for electrodepositing an electrocatalytic agent as referred to herein are, in principle, known in the art. As specified elsewhere herein, in an embodiment, the electrocatalytic agent is manganese, in particular is $MnO_2$. In such case, the electrocatalytic agent, i.e. $MnO_2$, may e.g. be electrodeposited from an aqueous solution of manganese sulphate. Suitable pHs and voltages for electrodeposition of a metal or a particular salt thereof can be derived from e.g. a Pourbaix graph. In an embodiment, deposition is performed potentiostatically, i.e. by applying a constant voltage. The skilled person knows how to determine appropriate conditions for electrodeposition, in particular voltages for potentiostatic deposition, e.g. as shown in the Examples. E.g., in an embodiment, $MnO_2$ may be electrodeposited from a solution of $MnSO_4$ having a pH of from 3 to 8, in particular a pH of from 5 to 7, at a potential of 1 V to 4 V, in particular 3.0 V to 3.5 V versus an Ag/AgCl electrode. In a further embodiment, deposition is performed galvanostatically, i.e. by adjusting the current such that an appropriate deposition rate is achieved, which is, in an embodiment, constant over the deposition time. In an embodiment, galvanostatic deposition is optimized by deriving an optimal current range from a current/potential curve established for the deposition process. As will be understood by the skilled person, the amount of electrodeposited material, in an embodiment layer thickness, can be controlled by adjusting deposition current and/or deposition time. In an embodiment, as shown in the Examples, $MnO_2$ can be deposited from a solution of Mn(II) ions, in particular $MnSO_4$ or $MnCl_2$ at a constant current of from 1 µA to 15 µA, in an embodiment of from 4 to 12.5 µA. In a further embodiment, as shown in the examples, Ag can be deposited from a solution of Ag(I) ions, in particular $AgNO_3$, at a constant current of from 10 µA to 300 µA, in an embodiment of from 25 µA to 275 µA. As is understood by the skilled person, the current suitable for electrodeposition to a specific electrode depends on a variety of further parameters, including area of the electrode, electrode geometry, geometry of the electric field applied, in particular relative positioning of the counter electrode, and the like.

The term "enzyme", as used herein, relates to a biological macromolecule, in particular a polypeptide, catalyzing in the presence of an analyte a chemical reaction producing or consuming a compound, the electrochemical conversion of which is catalyzed by the electrocatalytic agent as specified elsewhere herein. In an embodiment, the enzyme is an oxidase; in a further embodiment, the enzyme produces a peroxide in the presence of an analyte, in particular produces hydrogen peroxide; thus, in an embodiment, the enzyme is a hydrogen peroxide producing oxidase, e.g. a glucose oxidase (EC 1.1.3.4), hexose oxidase (EC 1.1.3.5), cholesterol oxidase (EC 1.1.3.6), galactose oxidase (EC 1.1.3.9), alcohol oxidase (EC 1.1.3.13), L-gulonolactone oxidase (EC 1.1.3.8), NAD(P)H oxidase (H2O2-forming, EC 1.6.3.1), NADH oxidase (H2O2-forming, EC 1.6.3.3) or catalase (EC 1.11.1.6). In an embodiment, the enzyme is glucose oxidase (EC 1.1.3.4).

The term "enzyme layer", as used herein, relates to a layer comprising an enzyme as specified herein above. In an embodiment, the enzyme layer comprises further components, in particular a further polypeptide, e.g. a carrier protein which may be applied in a substantially fixed ratio with the enzyme. The term "carrier protein", as used herein, relates to a protein or a mixture of proteins lacking at least a catalytic activity producing a compound determinable by the biosensor of the invention; in particular, the carrier protein does not have a known enzymatic activity and/or is a heat-inactivated protein. In an embodiment, the enzyme and the carrier protein are distributed in a substantially uniform manner throughout the enzyme layer. Typically the enzyme layer is thin, e.g. having a thickness of from 1 µm to 10 µm, in an embodiment of from 2 µm to 5 µm. Enzyme layers of this thickness may e.g. be manufactured by electrodeposition or by screen printing. As will be understood, in particular for screen printing an enzyme layer, the enzyme may be dispersed in a composition comprising further additives, including fillers, solvents, adherence mediators, and the like well known in the art. In a typical embodiment, the enzyme layer is very thin, e.g. having a thickness of about 1 µm, about 0.5 µm, about 0.25 µm or about 0.1 µm. Enzyme layers of such thickness may be obtained by dispensing or by spraying the enzyme and, potentially, additives which may be present dissolved in an appropriate solvent, e.g. water or an aqueous buffer.

The biosensor may further comprise at least one electrically insulating material. The electrically insulating material may be applied to the substrate, such as by coating the substrate with one or more layers of the at least one electrically insulating material. As an example, electrically insulating material may comprise one or more electrically insulating resins. Thus, the substrate may fully or partially be coated with one or more layers of the electrically insulating resin. Additionally or alternatively, other types of insulating materials fully or partially covering the substrate may be used. The at least one electrically insulating material may be applied directly or indirectly to the substrate, such as by coating techniques. Again, additionally or alternatively, the electrically insulating material may be part of the substrate itself. Thus, the substrate itself may fully or partially be made of at least one electrically insulating material. As an example, the substrate may fully or partially be made of an insulating plastic material such as an insulating polyester and/or may fully or partially be made of an insulating material such as paper and/or an insulating ceramic material.

Advantageously, it was found during the work underlying the present invention, that a mediator layer like $MnO_2$ may be electrodeposited onto a working electrode of a biosensor and that such electrodeposition leads to a homogenous, tightly adhering layer with a large surface. Also, the technical effort connected to screen printing said layer can be saved. Moreover, since the new method does not require use of a screen printing paste including DEGMBE, there are no peroxidized ethers present in the mediator layer and, thus, zero currents of the new sensors are very low. For the same reason, the new biosensors also do not require a prerun. Moreover, the using the method of the present invention, the size of a working electrode can be more exactly defined, since variability caused by screen printing is avoided. Moreover, the amount of deposited mediator can be more exactly defined during galvanic deposition. Thus, inter-lot variability of, e.g. analyte test strips, can be reduced.

The definitions made above apply mutatis mutandis to the following. Additional definitions and explanations made further below also apply for all embodiments described in this specification mutatis mutandis.

The present invention also relates to a method for manufacturing a biosensor, comprising
    a) providing a substrate having at least one conductive pad,
    b) electrodepositing a mediator layer onto at least part of said conductive pad, wherein said mediator layer comprises, in an embodiment consists of, an electrocatalytic agent, and
    c) depositing an enzyme layer onto at least part of said mediator layer.

The method for manufacturing of the present invention, in an embodiment, may comprise steps in addition to those explicitly mentioned above. For example, further steps may relate, e.g., to plating a conductive pad onto a substrate for step a), or applying further layer in, before, or after step b). Moreover, one or more of said steps may be performed by automated equipment. Moreover, the method for manufacturing may additionally comprise applying a coating technique, e.g. one or more of the following techniques: a printing technique; a dispensing technique. The printing technique may comprise an arbitrary printing technique, such as screen printing, in-jet printing, stencil printing, offset printing, tampon printing or any other printing technique or any arbitrary combination thereof. Additionally or alternatively, other coating techniques may be employed.

Moreover, the method for manufacturing may comprise further steps, such as at least one further step of providing least one conductive pad and/or at least one counter electrode conductive path on the substrate, applying a coating wherein an additional layer is applied to a conductive pad and/or wherein a counter electrode material is applied to the counter electrode conductive pad by at least one coating technique, such as by at least one printing technique and/or at least one dispensing technique. In case a printing technique is used, the at least one printing technique may comprise one or more different types of printing techniques. In an embodiment, the printing technique comprises at least one screen printing technique. The reference material and/or the counter electrode material, as out-lined above, may be applied as a paste. The reference material and/or the counter electrode material may further be coated into one or more openings of an electrically insulating material, such as by at least one of a printing technique and a dispensing technique, such as by screen printing. Additionally or alternatively, an insulating material may be applied after coating, such as after printing and/or dispensing, of the electrically conductive sensor material and/or the electrically conductive counter electrode material, respectively.

Further, the present invention relates to a biosensor produced or producible according to the method for manufacture of the present invention.

Moreover, the present invention relates to the use of a biosensor according to the present invention for determining an analyte in a sample.

Furthermore, the present invention relates to a method for detecting an analyte in a sample, comprising
    a) contacting said sample to an enzyme layer of a biosensor,
    said biosensor comprising a substrate, a working electrode comprising an electrically conductive pad in conductive contact with an electrodeposited mediator layer comprising, in an embodiment consisting of, an electrocatalytic agent, an enzyme layer in diffusion-enabling contact with said mediator layer, and at least one counter electrode,
    b) closing an electrical circuit comprising said working electrode, said mediator layer, and said counter electrode,
    c) applying a voltage to the electrical circuit of step b), measuring the resulting current, and, thereby,
    d) detecting said analyte in said sample.

The method for detecting of the present invention may be an in vitro method, performed on a sample from a subject, or an in vivo method, in case the biosensor is implanted into the body of a subject. Moreover, the method for detecting may comprise steps in addition to those explicitly mentioned above. For example, further steps may relate, e.g., to obtaining a sample or implanting the biosensor for step a), or performing calibrations and/or calculations on the values obtained in step c). Moreover, one or more of said steps may be performed by automated equipment.

As used herein, the term "subject" relates to a vertebrate. In an embodiment, the subject is a mammal, in a further embodiment, a mouse, rat, cat, dog, hamster, guinea pig, sheep, goat, pig, cattle, or horse. Still in a further embodiment, the subject is a primate. In a further embodiment, the subject is a human. In an embodiment, the subject is afflicted or suspected to be afflicted with a disease or condition associated with a measurable deviation from normal of at least one analyte. In a further embodiment, the subject is a subject afflicted with or suspected to be afflicted with diabetes, in particular diabetes type II.

The method for detecting of the invention may further comprise an amperometric measurement, e.g. when a sample containing an analyte is contacted with the biosensor, analyte, enzyme, and the electrocatalytic agent participate in a reaction, wherein the analyte is either reduced (receives at least one electron) or is oxidized (donates at least one electron). Typically, the analyte is oxidized. After this reaction is complete, an electrical potential difference can be applied between the working electrode and the counter electrode. Thus, in an embodiment, after start of the reaction, a power source (e.g., battery) is used to apply a potential difference between the electrodes and, e.g. a steady state assay current is measured by a current measuring meter.

The measured current may be correlated to the concentration of analyte; e.g. the magnitude of the current, in particular as measured at a quasi-steady-state condition, can be correlated to the amount of reaction product present, and, consequently, to the amount of analyte in the sample. The potential difference applied is selected such that electrooxidation of at least one reaction product occurs at the surface of the working electrode. The working electrode according to the present invention is in close contact, in an embodiment in direct contact, with the mediator layer of the biosensor; thus, the reaction product can be rapidly oxidized or reduced at the working electrode. In general, analytes, enzymes, and their reaction products are those as specified herein above. In an embodiment, the biosensor is a biosensor according to the present invention.

All references cited in this specification are herewith incorporated by reference with respect to their entire disclosure content and the disclosure content specifically mentioned in this specification.

In view of the above, the following embodiments are preferred:

Embodiment 1: A biosensor for determining an analyte comprising a substrate, a working electrode comprising an electrically conductive pad in conductive contact with a mediator layer, and an enzyme layer in diffusion-enabling contact with said mediator layer, wherein said mediator layer is an electrodeposited mediator layer, and wherein said mediator layer comprises, in an embodiment consists of, an electrocatalytic agent.

Embodiment 2: The biosensor according to embodiment 1, wherein said electrocatalytic agent is an agent catalyzing at least one electrochemical reaction by, in an embodiment selectively, decreasing the overpotential required for said electrochemical reaction to occur and/or by increasing the rate at which said electrochemical reaction occurs.

Embodiment 3: The biosensor according to embodiment 1 or 2, wherein said electrocatalytic agent comprises manganese, in an embodiment in ionic form.

Embodiment 4: The biosensor according to any one of embodiments 1 to 3, wherein said electrocatalytic agent comprises manganese(IV)-oxide (MnO2).

Embodiment 5: The biosensor according to any one of embodiments 1 to 4, wherein said mediator layer consists of manganese and/or of MnO2, in an embodiment consists of MnO2.

Embodiment 6: The biosensor according to any one of embodiments 1 to 5, wherein said mediator layer is free of organic ether peroxides, in an embodiment is free of organic ethers, in a further embodiment is free of organic solvents.

Embodiment 7: The biosensor according to any one of embodiments 1 to 6, wherein said working electrode comprises a multiplicity of electrically conductive pads, of which at least one, in an embodiment at least two, in a further embodiment half, in a further embodiment all, are in conductive contact with a mediator layer being in diffusion-enabling contact with an enzyme layer.

Embodiment 8: The biosensor according to any one of embodiments 1 to 7, wherein said biosensor further comprises a counter electrode, in an embodiment further comprises a reference electrode and a counter electrode.

Embodiment 9: The biosensor according to embodiment 8, wherein said counter electrode is situated on the opposite side of said substrate relative to the working electrode.

Embodiment 10: The biosensor according to embodiment 8 or 9, wherein said reference electrode comprises a layer of reference material.

Embodiment 11: The biosensor according to embodiment 10, wherein said reference material is electrodeposited.

Embodiment 12: The biosensor according to embodiment 10 or 11, wherein said reference material comprises at least one of the metals silver (Ag), copper (Cu), manganese (Mn), lead (Pb), quicksilver (Hg), nickel (Ni), cobalt (Co), bismuth (Bi), Rhenium (Re), and Tellurium (Te), in an embodiment comprises one of said metals.

Embodiment 13: The biosensor according to any one of embodiments 10 to 12, wherein said reference material comprises said at least one metal in ionic and/or in elemental form.

Embodiment 14: The biosensor according to any one of embodiments 10 to 13, wherein said reference material comprises silver, in an embodiment comprises silver chloride.

Embodiment 15: The biosensor according to any one of embodiments 1 to 14, wherein said enzyme layer comprises an enzyme producing a peroxide in the presence of an analyte.

Embodiment 16: The biosensor according to any one of embodiments 1 to 15, wherein said peroxide is hydrogen peroxide.

Embodiment 17: The biosensor according to any one of embodiments 1 to 16, wherein said analyte is glucose.

Embodiment 18: The biosensor according to any one of embodiments 1 to 17, wherein said enzyme layer comprises glucose oxidase.

Embodiment 19: The biosensor according to any one of embodiments 1 to 18, wherein said biosensor is an electrochemical biosensor.

Embodiment 20: The biosensor according to any one of embodiments 1 to 19, wherein said biosensor is an implantable biosensor.

Embodiment 21: The biosensor according to any one of embodiments 1 to 20, wherein said biosensor further comprises a diffusion membrane.

Embodiment 22: The biosensor according to any one of embodiments 1 to 21, wherein said biosensor further comprises a biocompatibility layer.

Embodiment 23: The biosensor according to any one of embodiments 1 to 22, wherein said conductive pad comprises at least one gold layer, in an embodiment consists of gold, in a further embodiment consists of electrodeposited gold.

Embodiment 24: The biosensor according to any one of embodiments 1 to 23, wherein said conductive contact and/or said diffusion-enabling contact is direct contact.

Embodiment 25: A method for manufacturing a biosensor, comprising providing a substrate having at least one conductive pad a) electrodepositing a mediator layer onto at least part of said conductive pad, wherein said mediator layer comprises, in an embodiment consists of, an electrocatalytic agent, and b) depositing an enzyme layer onto at least part of said mediator layer.

Embodiment 26: The method of embodiment 25, wherein said mediator layer comprises manganese, in an embodiment in ionic form.

Embodiment 27: The method of embodiment 25 or 26, wherein said mediator layer comprises manganese(IV)-oxide (MnO2).

Embodiment 28: The method of any one of embodiments 25 to 26, wherein said mediator layer consists of manganese or of MnO2, in an embodiment consists of MnO2.

Embodiment 29: The method of any one of embodiments 25 to 27, wherein said method comprises providing a substrate further comprising at least one of a reference electrode and a counter electrode, in an embodiment further comprising a reference electrode and a counter electrode.

Embodiment 30: The method of any one of embodiments 25 to 29, wherein said biosensor further comprises depositing a diffusion membrane after depositing said enzyme layer.

Embodiment 31: The method of embodiment 29 or 30, wherein said method further comprises depositing a layer of reference material onto said reference electrode.

Embodiment 32: The method of any one of embodiments 29 to 31, wherein said method further comprises electrodepositing a layer of reference material onto said reference electrode.

Embodiment 33: The method of any one of embodiments 25 to 32, wherein depositing said enzyme layer comprises depositing an enzyme producing a peroxide in the presence of an analyte.

Embodiment 34: The method of any one of embodiments 25 to 33, wherein said enzyme layer is deposited by dispensing, by spraying, or by screen-printing.

Embodiment 35: A biosensor produced or producible according to the method of any one of embodiments 25 to 34.

Embodiment 36: Use of a biosensor according to any one of embodiments 1 to 24 for determining an analyte in a sample.

Embodiment 37: A method for detecting an analyte in a sample, comprising a) contacting said sample to an enzyme layer of a biosensor, said biosensor comprising a substrate, a working electrode comprising an electrically conductive pad in conductive contact with an electrodeposited mediator layer comprising, in an embodiment consisting of, an electrocatalytic agent, an enzyme layer in diffusion-enabling contact with said mediator layer, and at least one counter electrode, b) closing an electrical circuit comprising said working electrode, said mediator layer, and said counter electrode, c) applying a voltage to the electrical circuit of step b), measuring the resulting current, and, thereby, d) detecting said analyte in said sample.

Embodiment 38: The method of embodiment 37, wherein said biosensor is a biosensor according to any one of embodiments 1 to 24.

FIGURE LEGENDS

FIG. 1: Galvanostatic Chronoamperometry of Ag deposition at 250 µA in example 1. x-axis: time t (s); y-axis: potential $\Delta U$ (V).

Figure 2:
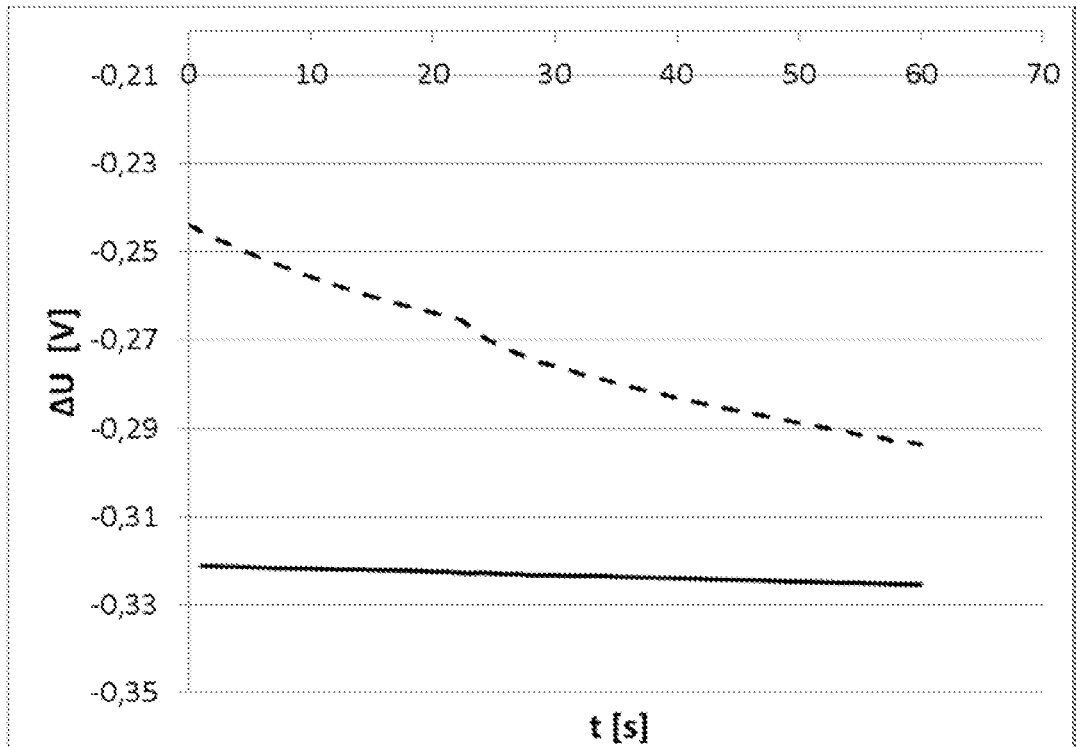

FIG. 2: Stability of the potential of an electrode produced by electrodeposition of silver, followed by electro-oxidation in chloride-containing solution. Shown is the potential vs. a $MnO_2$ electrode over time; dashed line: Ag only (before oxidation) solid line: AgCl (after oxidation). x-axis: time t (s); y-axis: potential $\Delta U$ (V).

Figure 3:
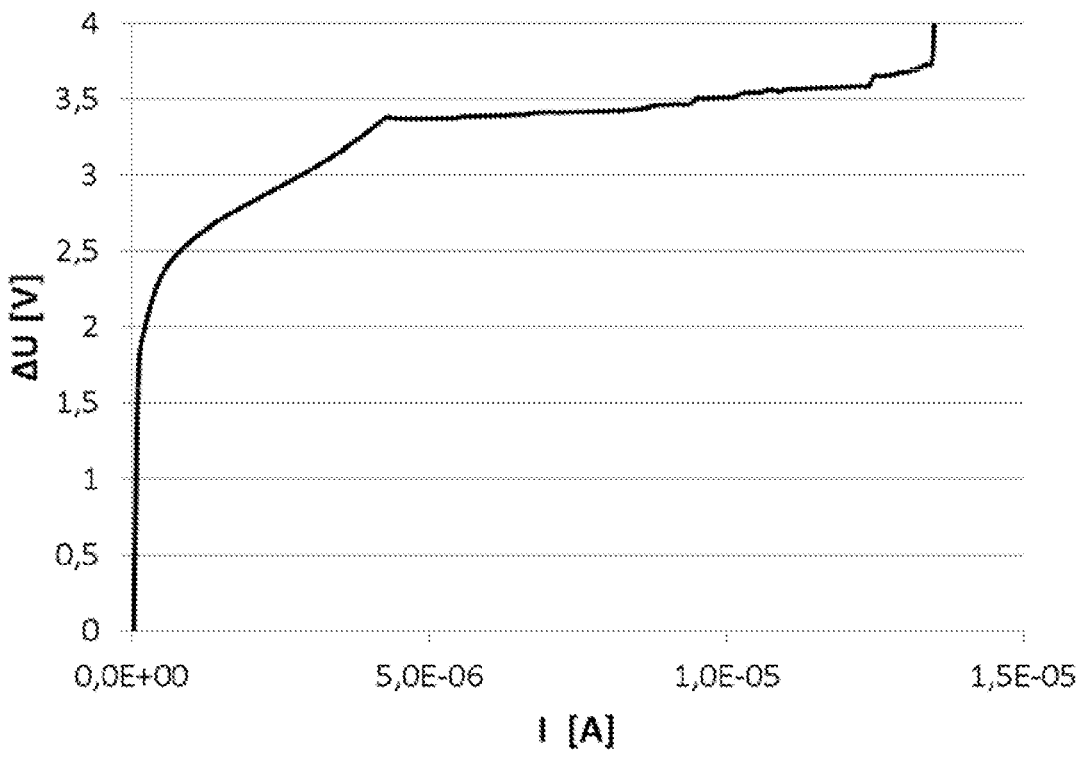

FIG. 3: Determining deposition voltage for depositing $MnO_2$ from a $MnSO_4$-solution; galvanostatic Cyclic Voltammogramm of $MnSO_4$ at a potential of 350 mV vs. Ag/AgCl/0.15 M Cl⁻. x-axis: current I (A); y-axis: potential $\Delta U$ (V).

Figure 4:
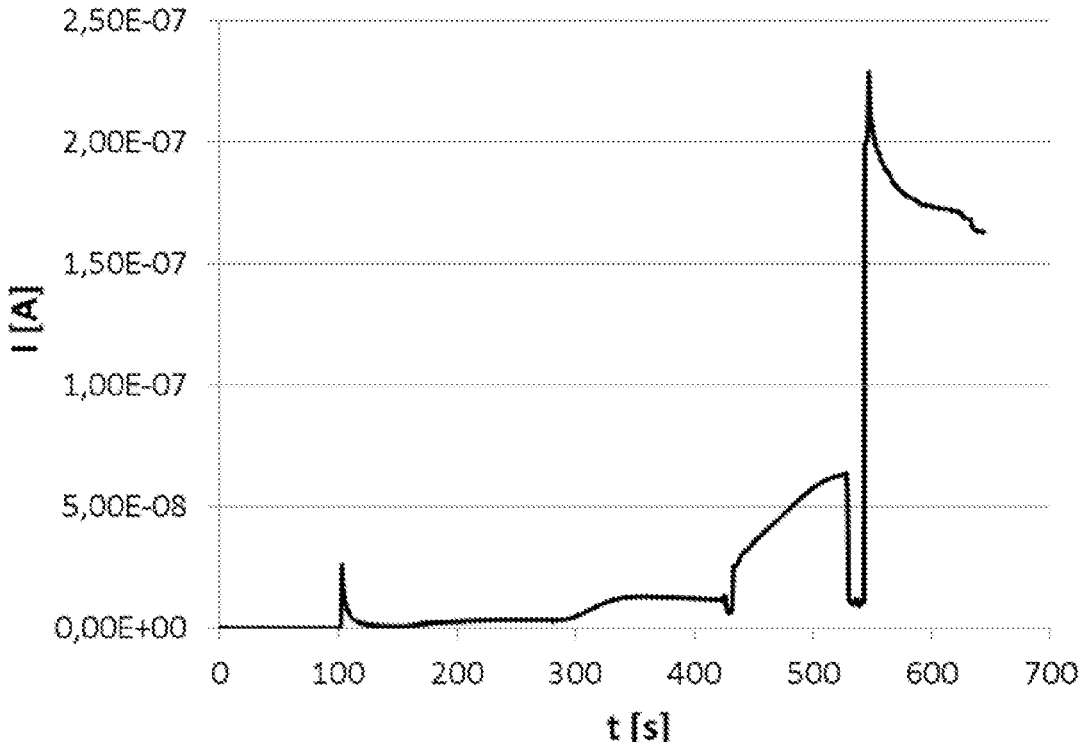

FIG. 4: Functionality of an electrodeposited $MnO_2$ layer in catalysis of electrochemical $H_2O_2$-oxidation. At time points 100 s, 280 s, 430 s, and 550 s, $H_2O_2$ was added, followed by sporadic mixing (100 s), moderate mixing (280 s), intensive mixing (430 s), and intensive mixing by inverting the whole sensor cell (550 s). x-axis: time t (s); y-axis: current I (A).

The following Examples shall merely illustrate the invention. They shall not be construed, whatsoever, to limit the scope of the invention.

EXAMPLE 1: SILVER DEPOSITION ON A SUBSTRATE: REFERENCE ELECTRODE

A 3-electrode setup was used (working electrode, reference electrode, counter electrode; all having Au-Pads) on an Autolab PGSTAT128N potentiostat/galvanostat. Using galvanostatic chronopotentiometry at −250 µA (FIG. 1), a particularly high rate of deposition of silver from a silver nitrate solution onto a gold electrode pad could be obtained; deposition starts at approximately −120 mV (vs. the Au-pseudo-reference in AgNO3 solution). The deposited shiny silver was visible in the microscope. The amount deposited was determined as: Charge Q=180 s×250 µA=45 mC; amount of substance n=Q/F=(45 E−3 C)/96484 C/mol=460 nmol. Accordingly, silver can be selectively galvanically deposited onto a reference electrode pad.

EXAMPLE 2: POTENTIAL STABILITY AFTER PARTIAL OXIDATION

To test usability as reference electrode, the Ag-coated reference electrode of Example 1 was tested for potential stability. The electrode initially showed the expected reference potential (approx. 275-325 mV vs. manganese dioxide) without oxidation; however, the potential was not stable. After a short (10 seconds) galvanostatic oxidation at 1 µA in a chloride-ion containing solution, the potential against $MnO_2$ was essentially constant. The ratio Ag/AgCl was adjusted via the amount of charge applied. In FIG. 2, 45 mC Ag deposition (Example 1) (dashed line) and only 10 µC oxidation to AgCl (solid line) were used, which reduced potential drift drastically.

EXAMPLE 3: $MNO_2$ DEPOSITION ON A SUBSTRATE: WORKING ELECTRODE $MnO_2$ was deposited onto multiple pads of a sensor electrode in a 2-electrode setup (working electrode, reference electrode/counter electrode, sensor reference electrode unused), using a galvanostatic CV from 0 to 15 µA (vs. reference electrode/counter electrode in Mn2+); deposition potential was 3.4 V with a disc voltage reference electrode=counter electrode at 2 V on sensor counter electrode (FIG. 3). Under these conditions, $MnO_2$ was deposited onto all working electrode pads. Accordingly, galvanically depositing $MnO_2$ is possible.

EXAMPLE 4: FUNCTIONALITY TESTING ($H_2O_2$-OXIDATION)

Functionality of the electrodeposited $MnO_2$ in $H_2O_2$-oxidation and functionality of the Ag/AgCl reference electrode were tested in chronoamperometry at 350 mV vs. sensor reference and addition of $H_2O_2$. As shown in FIG. 4, the sensor shows an $H_2O_2$-dependent signal at 350 mV. Notably, the zero current is very low (approx. 50 pA). Moreover, a running-in of zero current is not observed, since the galvanically deposited electrode does not contain ether peroxides from the paste solvent DEGMBE.

The invention claimed is:

1. A method for the in vivo electrochemical determination of a glucose analyte comprising:

transcutaneously implanting an in vivo biosensor beneath a patient's skin in contact with a bodily fluid comprising glucose, the in vivo biosensor comprising a substrate, a working electrode comprising a first electrically conductive pad, a counter and/or reference electrode comprising a second electrically conductive pad, a mediator layer electrodeposited on and in direct contact with the working electrode, the mediator layer consisting of manganese and/or $MnO_2$, and an enzyme layer in diffusion-enabling contact with the mediator layer, the enzyme layer comprising a glucose oxidase, the mediator layer and the enzyme layer being separate from each other;

closing an electrical circuit comprising the working electrode, the mediator layer, and the counter electrode;

applying a voltage to the electrical circuit;

measuring the resulting current; and determining the glucose analyte in the bodily fluid from the measured current.

2. The method of claim 1, comprising a method performing continuous monitoring of the glucose analyte.

3. The method of claim 1, wherein the working electrode comprises a multiplicity of electrically conductive pads, of which at least one is in direct contact with the mediator layer in diffusion-enabling contact with the enzyme layer.

4. The method of claim 1, wherein the biosensor comprises a layer of reference material.

5. The method of claim 4, wherein the reference material comprises silver.

6. The method of claim 1, wherein the mediator layer consists of $MnO_2$.

7. The method of claim 1, wherein the mediator layer separates the enzyme layer from the working electrode.

8. The method of claim 1, wherein the separate enzyme layer is deposited on the mediator layer.

9. The method of claim 1 in which the biosensor further comprises a diffusion membrane separating the working electrode, the mediator layer, and the counter electrode from the bodily fluid.

10. The method of claim 9 in which the biosensor further comprises an outmost layer comprising a biocompatible layer.

* * * * *